(12) United States Patent
Satish et al.

(10) Patent No.: US 10,424,060 B2
(45) Date of Patent: Sep. 24, 2019

(54) METHOD FOR ESTIMATING BLOOD COMPONENT QUANTITIES IN SURGICAL TEXTILES

(71) Applicant: Gauss Surgical, Inc., Los Altos, CA (US)

(72) Inventors: Siddarth Satish, Cupertino, CA (US); Kevin J. Miller, Mountain View, CA (US); Andrew T. Hosford, Mountain View, CA (US)

(73) Assignee: Gauss Surgical, Inc., Menlo Park, CA (US)

( * ) Notice: Subject to any disclaimer, the term of this patent is extended or adjusted under 35 U.S.C. 154(b) by 26 days.

(21) Appl. No.: 15/390,017

(22) Filed: Dec. 23, 2016

(65) Prior Publication Data

US 2017/0186160 A1     Jun. 29, 2017

Related U.S. Application Data

(60) Provisional application No. 62/387,222, filed on Dec. 23, 2015.

(51) Int. Cl.
   *G06T 7/00*           (2017.01)
   *A61B 5/02*           (2006.01)
   *G06K 9/46*           (2006.01)
   *A61B 5/00*           (2006.01)
   (Continued)

(52) U.S. Cl.
CPC .......... *G06T 7/0012* (2013.01); *A61B 5/0082* (2013.01); *A61B 5/02042* (2013.01); *G06K 9/4604* (2013.01); *G06K 9/4652* (2013.01); *G06K 9/6267* (2013.01); *G06T 7/62* (2017.01); *A61B 2505/05* (2013.01); *A61B 2576/02* (2013.01); *G06K 2209/05* (2013.01); *G06T 2207/10024* (2013.01); *G06T 2207/10028* (2013.01); *G06T 2207/10048* (2013.01); *G06T 2207/30004* (2013.01); *G06T 2207/30104* (2013.01); *G06T 2207/30242* (2013.01)

(58) Field of Classification Search
CPC ....... G06T 7/0012; G06T 7/62; A61B 5/0082; A61B 5/02042; G06K 9/4604; G06K 9/4652; G06K 9/6267
See application file for complete search history.

(56) References Cited

U.S. PATENT DOCUMENTS

| | | |
|---|---|---|
| 2,707,955 A | 5/1955 | Borden |
| 3,182,252 A | 5/1965 | van den Berg |
| 3,199,507 A | 8/1965 | Kamm |

(Continued)

FOREIGN PATENT DOCUMENTS

| | | |
|---|---|---|
| CA | 2870635 A1 | 10/2013 |
| CN | 101505813 A | 8/2009 |

(Continued)

OTHER PUBLICATIONS

Corrected Notice of Allowability dated Sep. 15, 2017, for U.S. Appl. No. 14/687,842, filed Apr. 15, 2015, 2 pages.

(Continued)

*Primary Examiner* — Utpal D Shah
(74) *Attorney, Agent, or Firm* — Cooley LLP

(57) ABSTRACT

Systems and methods for detecting, counting and analyzing the blood content of a surgical textile are provided, utilizing an infrared or depth camera in conjunction with a color image.

23 Claims, 7 Drawing Sheets

(51) Int. Cl.
  *G06K 9/62* (2006.01)
  *G06T 7/62* (2017.01)

(56) References Cited

U.S. PATENT DOCUMENTS

| | | |
|---|---|---|
| 3,367,431 A | 2/1968 | Prindle Baker |
| 3,646,938 A | 3/1972 | Haswell |
| 3,832,135 A | 8/1974 | Drozdowski et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,190,153 A | 2/1980 | Olsen |
| 4,244,369 A | 1/1981 | McAvinn et al. |
| 4,295,537 A | 10/1981 | McAvinn et al. |
| 4,313,292 A | 2/1982 | McWilliams |
| 4,402,373 A | 9/1983 | Comeau |
| 4,422,548 A | 12/1983 | Cheesman et al. |
| 4,429,789 A | 2/1984 | Puckett |
| 4,562,842 A | 1/1986 | Morfeld et al. |
| 4,583,546 A | 4/1986 | Garde |
| 4,642,089 A | 2/1987 | Zupkas et al. |
| 4,681,571 A | 7/1987 | Nehring |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,009,275 A | 4/1991 | Sheehan |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 6/1992 | Manion et al. |
| 5,190,059 A | 3/1993 | Fabian et al. |
| 5,227,765 A | 7/1993 | Ishizuka et al. |
| 5,231,032 A | 7/1993 | Ludvigsen |
| 5,236,664 A | 8/1993 | Ludvigsen |
| 5,285,682 A | 2/1994 | Micklish |
| 5,348,533 A | 9/1994 | Papillon et al. |
| 5,369,713 A | 11/1994 | Schwartz et al. |
| 5,443,082 A | 8/1995 | Mewburn |
| 5,492,537 A | 2/1996 | Vancaillie |
| 5,522,805 A | 6/1996 | Vancaillie et al. |
| 5,629,498 A | 5/1997 | Pollock et al. |
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,640,130 B1* | 10/2003 | Freeman .............. A61B 5/0059 382/128 |
| 6,641,039 B2 | 11/2003 | Southard |
| 6,699,231 B1 | 3/2004 | Sterman et al. |
| 6,728,561 B2 | 4/2004 | Smith et al. |
| 6,730,054 B2 | 5/2004 | Pierce et al. |
| 6,763,148 B1 | 7/2004 | Sternberg et al. |
| 6,777,623 B2 | 8/2004 | Ballard |
| 6,781,067 B2 | 8/2004 | Montagnino |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,255,003 B2 | 8/2007 | Schneiter |
| 7,274,947 B2 | 9/2007 | Koo et al. |
| 7,297,834 B1 | 11/2007 | Shapiro |
| 7,299,981 B2 | 11/2007 | Hickle et al. |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | Mccall |
| D611,731 S | 3/2010 | Levine |
| 7,670,289 B1 | 3/2010 | Mccall |
| 7,703,674 B2 | 4/2010 | Stewart |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,872,201 B1 | 1/2011 | Whitney |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,241,238 B2 | 8/2012 | Hiruma et al. |
| 8,279,068 B2 | 10/2012 | Morris et al. |
| 8,374,397 B2 | 2/2013 | Shpunt et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,639,226 B2 | 1/2014 | Hutchings et al. |
| 8,693,753 B2 | 4/2014 | Nakamura |
| 8,704,178 B1 | 4/2014 | Pollock et al. |
| 8,768,014 B2 | 7/2014 | Du et al. |
| 8,792,693 B2 | 7/2014 | Satish et al. |
| 8,823,776 B2 | 9/2014 | Tian et al. |
| 8,897,523 B2 | 11/2014 | Satish et al. |
| 8,983,167 B2 | 3/2015 | Satish et al. |
| 8,985,446 B2 | 3/2015 | Fleck et al. |
| 9,047,663 B2* | 6/2015 | Satish .................. A61M 1/0001 |
| 9,171,368 B2 | 10/2015 | Satish et al. |
| 9,347,817 B2 | 5/2016 | Pollock et al. |
| 9,595,104 B2 | 3/2017 | Satish et al. |
| 9,652,655 B2* | 5/2017 | Satish ...................... G06K 9/00 |
| 9,824,441 B2 | 11/2017 | Satish et al. |
| 9,936,906 B2* | 4/2018 | Satish ................ A61B 5/14535 |
| 2003/0069425 A1 | 4/2003 | Matzinger et al. |
| 2003/0095197 A1 | 5/2003 | Wheeler et al. |
| 2003/0130596 A1 | 7/2003 | Von Der Goltz |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1 | 7/2005 | Ziegler |
| 2005/0265996 A1 | 12/2005 | Lentz |
| 2006/0058593 A1 | 3/2006 | Drinan et al. |
| 2006/0178578 A1 | 8/2006 | Tribble et al. |
| 2006/0224086 A1 | 10/2006 | Harty |
| 2007/0004959 A1 | 1/2007 | Carrier et al. |
| 2007/0024946 A1 | 2/2007 | Panasyuk et al. |
| 2007/0108129 A1 | 5/2007 | Mori et al. |
| 2007/0243137 A1 | 10/2007 | Hainfeld |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0080757 A1 | 3/2009 | Roger et al. |
| 2009/0257632 A1 | 10/2009 | Lalpuria et al. |
| 2009/0310123 A1 | 12/2009 | Thomson |
| 2009/0317002 A1 | 12/2009 | Dein |
| 2010/0003714 A1 | 1/2010 | Bachur |
| 2010/0007727 A1 | 1/2010 | Torre-Bueno |

(56) References Cited

U.S. PATENT DOCUMENTS

| | | |
|---|---|---|
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0087770 A1 | 4/2010 | Bock |
| 2010/0150759 A1 | 6/2010 | Mazur et al. |
| 2010/0280117 A1 | 11/2010 | Patrick et al. |
| 2011/0066182 A1 | 3/2011 | Falus |
| 2011/0118647 A1 | 5/2011 | Paolini et al. |
| 2011/0192745 A1 | 8/2011 | Min |
| 2011/0196321 A1 | 8/2011 | Wudyka |
| 2011/0200239 A1 | 8/2011 | Levine et al. |
| 2011/0275957 A1 | 11/2011 | Bhandari |
| 2011/0305376 A1 | 12/2011 | Neff |
| 2011/0316973 A1 | 12/2011 | Miller et al. |
| 2012/0000297 A1 | 1/2012 | Hashizume et al. |
| 2012/0064132 A1 | 3/2012 | Aizawa et al. |
| 2012/0065482 A1 | 3/2012 | Robinson et al. |
| 2012/0106811 A1 | 5/2012 | Chen et al. |
| 2012/0127290 A1 | 5/2012 | Tojo et al. |
| 2012/0210778 A1 | 8/2012 | Palmer et al. |
| 2012/0257188 A1 | 10/2012 | Yan et al. |
| 2012/0262704 A1 | 10/2012 | Zahniser et al. |
| 2012/0309636 A1 | 12/2012 | Gibbons et al. |
| 2012/0327365 A1 | 12/2012 | Makihira |
| 2013/0011031 A1 | 1/2013 | Satish et al. |
| 2013/0011042 A1* | 1/2013 | Satish ............... G06K 9/00 382/134 |
| 2013/0034908 A1 | 2/2013 | Barstis et al. |
| 2013/0088354 A1 | 4/2013 | Thomas |
| 2013/0094996 A1 | 4/2013 | Janssenswillen |
| 2013/0170729 A1 | 7/2013 | Wardlaw et al. |
| 2013/0301901 A1 | 11/2013 | Satish et al. |
| 2013/0303870 A1* | 11/2013 | Satish ............... A61B 5/14535 600/371 |
| 2013/0308852 A1 | 11/2013 | Hamsici et al. |
| 2014/0079297 A1 | 3/2014 | Tadayon et al. |
| 2014/0207091 A1 | 7/2014 | Heagle et al. |
| 2014/0294237 A1 | 10/2014 | Litvak et al. |
| 2014/0330094 A1 | 11/2014 | Pacione et al. |
| 2015/0294460 A1 | 10/2015 | Satish et al. |
| 2015/0310634 A1 | 10/2015 | Babcock et al. |
| 2016/0069743 A1* | 3/2016 | McQuilkin ............ G01J 3/2803 356/416 |
| 2016/0123998 A1 | 5/2016 | MacIntyre et al. |
| 2016/0331248 A1 | 11/2016 | Satish et al. |
| 2016/0331282 A1 | 11/2016 | Satish et al. |
| 2017/0011276 A1 | 1/2017 | Mehring et al. |
| 2017/0023446 A1 | 1/2017 | Rietveld et al. |
| 2017/0351894 A1 | 12/2017 | Satish et al. |
| 2017/0352152 A1 | 12/2017 | Satish et al. |
| 2018/0199827 A1 | 7/2018 | Satish et al. |
| 2019/0008427 A1 | 1/2019 | Satish et al. |

FOREIGN PATENT DOCUMENTS

| | | |
|---|---|---|
| JP | S-59-161801 U | 10/1984 |
| JP | S-61-176357 A | 8/1986 |
| JP | S-62-144652 U | 6/1987 |
| JP | H-06-510210 A | 11/1994 |
| JP | H-07-308312 A | 11/1995 |
| JP | H-11-37845 A | 2/1999 |
| JP | 2000-227390 A | 8/2000 |
| JP | 2002-331031 A | 11/2002 |
| JP | 2003-075436 A | 3/2003 |
| JP | 2005-052288 A | 3/2005 |
| JP | 3701031 B2 | 9/2005 |
| JP | 2006-280445 A | 10/2006 |
| JP | 2007-101482 | 4/2007 |
| JP | 2008-055142 A | 3/2008 |
| JP | 2008-519604 A | 6/2008 |
| JP | 2010-516429 A | 5/2010 |
| JP | 2011-036371 A | 2/2011 |
| JP | 2011-515681 A | 5/2011 |
| JP | 2011-252804 A | 12/2011 |
| WO | WO-92/17787 A1 | 10/1992 |
| WO | WO-1996/039927 A1 | 12/1996 |
| WO | WO-2006/053208 A1 | 5/2006 |
| WO | WO-2008/094703 A2 | 8/2008 |
| WO | WO-2008/094703 A3 | 8/2008 |
| WO | WO-2009/117652 A1 | 9/2009 |
| WO | WO-2011/019576 A1 | 2/2011 |
| WO | WO-2011/145351 A1 | 11/2011 |
| WO | WO-2013/009709 A2 | 1/2013 |
| WO | WO-2013/009709 A3 | 1/2013 |
| WO | WO-2013/138356 A2 | 9/2013 |
| WO | WO-2013/138356 A3 | 9/2013 |
| WO | WO-2013/172874 A1 | 11/2013 |
| WO | WO-2013/173356 A1 | 11/2013 |
| WO | WO-2014/025415 A2 | 2/2014 |
| WO | WO-2014/025415 A3 | 2/2014 |
| WO | WO-2015/160997 A1 | 10/2015 |

OTHER PUBLICATIONS

Non-Final Office Action dated Apr. 11, 2018, for U.S. Appl. No. 15/416,986, filed Jan. 26, 2017, 7 pages.
Notice of Allowance dated Nov. 20, 2017, for U.S. Appl. No. 13/894,054, filed May 14, 2013, 8 pages.
U.S. Appl. No. 15/943,561, filed Apr. 2, 2018, by Satish et al.
ACOG (2012). "Optimizing protocols in obstetrics," Series 2, 25 total pages.
Adkins, A.R. et al. (2014). "Accuracy of blood loss estimations among anesthesia providers," *AANA Journal* 82(4):300-306.
Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>, 6 pages.
Al-Kadri, H.M. et al. (2014). "Effect of education and clinical assessment on the accuracy of post partum blood loss estimation," *BMC Preg. Childbirth* 14:110, 7 total pages.
AWHONN Practice Brief (2014). "Quantification of blood loss: AWHONN practice brief No. 1," *AWHONN* p. 1-3.
Bellad, et al. (2009). "Standardized Visual Estimation of Blood Loss during Vaginal Delivery with Its Correlation Hematocrit Changes—A Descriptive Study." South Asian Federation of Obstetrics and Gynecology 1:29-34.
Bose, P. et al. (2006). "Improving the accuracy of estimated blood loss at obstetric haemorrhage using clinical reconstructions," *BJOG* 113(8):919-924.
Eipe, N. et al. (2006). "Perioperative blood loss assessment—How accurate?" *Indian J. Anaesth.* 50(1):35-38.
Extended European Search Report dated Apr. 1, 2015, for EP Application No. 12 810 640.8, filed on Jul. 9, 2012, 8 pages.
Extended European Search Report dated Nov. 23, 2015, for EP Application No. 13 790 688.9, filed on May 14, 2013, 9 pages.
Extended European Search Report dated Nov. 17, 2015, for EP Application No. 13 790 449.6, filed on Jan. 10, 2013, 8 pages.
Extended European Search Report dated Nov. 4, 2016, for EP Application No. 16 183 350.4, filed on Jul. 9, 2012, 9 pages.
Extended European Search Report dated Jul. 26, 2017, for EP Application No. 15 780 653.0, filed on Apr. 15, 2015, 12 pages.
Final Office Action dated Feb. 12, 2016, for U.S. Appl. No. 13/544,664, filed Jul. 9, 2012, 9 pages.
Final Office Action dated Aug. 26, 2016, for U.S. Appl. No. 13/894,054, filed May 14, 2013, 7 pages.
Final Office Action dated Jul. 26, 2016, for U.S. Appl. No. 14/876,628, filed Oct. 6, 2015, 5 pages.
Habak, P.J. et al. (2016). "A comparison of visual estimate versus calculated estimate of blood loss at vaginal delivery," *British J. Med. Medical Res.* 11(4):1-7.
Holmes, A.A. et al. (2014). "Clinical evaluation of a novel system for monitoring surgical hemoglobin loss," *Anesth. Analg.* 119(3):588-594.
International Search Report dated Sep. 17, 2012, for PCT Application No. PCT/US2012/045969, filed on Jul. 9, 2012, 2 pages.
International Search Report dated Sep. 24, 2013, for PCT Application No. PCT/US2013/040976, filed on May 14, 2013, 2 pages.

(56) References Cited

OTHER PUBLICATIONS

International Search Report dated Mar. 26, 2013, for PCT Application No. PCT/US2013/021075, filed on Jan. 10, 2013, 2 pages.
International Search Report dated Jul. 24, 2015, for PCT Application No. PCT/US2015/026036, filed on Apr. 15, 2015, 2 pages.
International Search Report dated Mar. 30, 2017, for PCT Application No. PCT/US2016/068540, filed on Dec. 23, 2016, 3 pages.
Jones, R. (2015). "Quantitative measurement of blood loss during delivery," *AWHONN* p. S41.
Kamiyoshihara, M. et al. (2008). "The Utility of an Autologous Blood Salvage System in Emergency Thoracotomy for a Hemothorax After Chest Trauma," *Gen. Thorac. Cardiovasc. Surg.* 56:222.
Lyndon, A. et al. (2010). "Blood loss: Clinical techniques for ongoing quantitative measurement," *CMQCC Obstetric Hemorrhage Toolkit*, pp. 1-7.
Lyndon, A. et al. (2015). "Cumulative quantitative assessment of blood loss," *CMQCC Obstetric Hemorrhage Toolkit Version* 2.0, pp. 80-85.
Manikandan, D. et al. (2015). "Measurement of blood loss during adenotonsillectomy in children and factors affecting it," *Case Reports in Clinical Medicine* 4:151-156.
Merck for Mother's Program (2012). Blood loss measurement: Technology opportunity assessment, 9 total pages.
Non-Final Office Action dated Aug. 13, 2015, for U.S. Appl. No. 13/544,664, filed Jul. 9, 2012, 8 pages.
Non-Final Office Action dated Aug. 2, 2016, for U.S. Appl. No. 13/544,664, filed Jul. 9, 2012, 6 pages.
Non-Final Office Action dated May 9, 2014, for U.S. Appl. No. 13/544,679, filed Jul. 9, 2012, 7 pages.
Non-Final Office Action dated Mar. 30, 2016, for U.S. Appl. No. 13/894,054, filed May 14, 2013, 9 pages.
Non-Final Office Action dated Sep. 5, 2014, for U.S. Appl. No. 13/738,919, filed Jan. 10, 2013, 8 pages.
Non-Final Office Action dated Mar. 20, 2015, for U.S. Appl. No. 14/613,807, filed Feb. 4, 2015, 8 pages.
Non-Final Office Action dated Dec. 15, 2015, for U.S. Appl. No. 14/876,628, filed Oct. 6, 2015, 8 pages.
Non-Final Office Action dated Mar. 24, 2017, for U.S. Appl. No. 14/687,842, filed Apr. 15, 2015, 28 pages.
Non-Final Office Action dated Apr. 20, 2017, for U.S. Appl. No. 13/894,054, filed May 14, 2013, 7 pages.
Notice of Allowance dated May 12, 2014, for U.S. Appl. No. 13/544,646, filed Jul. 9, 2012, 10 pages.
Notice of Allowance dated Sep. 3, 2014, for U.S. Appl. No. 13/544,679, filed Jul. 9, 2012, 8 pages.
Notice of Allowance dated Nov. 10, 2014, for U.S. Appl. No. 13/738,919, filed Jan. 10, 2013, 10 pages.
Notice of Allowance dated Jun. 25, 2015, for U.S. Appl. No. 14/613,807, filed Feb. 4, 2015, 10 pages.
Notice of Allowance dated Oct. 26, 2016, for U.S. Appl. No. 14/876,628, filed Oct. 6, 2015, 11 pages.
Notice of Allowance dated Feb. 15, 2017, for U.S. Appl. No. 13/544,664, filed Jul. 9, 2012, 10 pages.
Notice of Allowance dated Aug. 3, 2017, for U.S. Appl. No. 14/687,842, filed Apr. 15, 2015, 9 pages.
Pogorelc, D. iPads in the OR: New Mobile Platform to Monitor Blood Loss During Surgery. MedCityNews, Jun. 6, 2012. http://medcitynews.com/2012/06/ipads-in-the-or-new-mobile-platform-to-monitor-blood-loss-during-surgery, 4 pages.
Roston, A.B. et al. (2012). "Chapter 9: Blood loss: Accuracy of visual estimation," in *A comprehensive textbook of postpartum hemorrhage: An essential clinical reference for effective management*, $2^{nd}$ edition, Sapiens publishing, pp. 71-72.
Sant, et al. "Exsanguinated Blood Volume Estimation Using Fractal Analysis of Digital Images." Journal of Forensic Sciences 57.3 (2012): 610-17.
Schorn, M.N. (2010). "Measurement of blood loss: Review of the literature," *J. Midwifery and Women's Health* 55(1):20-27.
Sukprasert, M. et al. (2006). "Increase accuracy of visual estimation of blood loss from education programme," *J. Med. Assoc. Thai* 89(suppl. 4):S54-S59.
Written Opinion of the International Searching Authority dated Sep. 17, 2012, for PCT Application No. PCT/US2012/045969, filed on Jul. 9, 2012, 4 pages.
Written Opinion of the International Searching Authority dated Sep. 24, 2013, for PCT Application No. PCT/US2013/040976, filed on May 14, 2013, 4 pages.
Written Opinion of the International Searching Authority dated Mar. 26, 2013, for PCT Application No. PCT/US2013/021075, filed on Jan. 10, 2013, 6 pages.
Written Opinion of the International Searching Authority dated Jul. 24, 2015, for PCT Application No. PCT/US2015/026036, filed on Apr. 15, 2015, 6 pages.
Written Opinion of the International Searching Authority dated Mar. 30, 2017, for PCT Application No. PCT/US2016/068540, filed on Dec. 23, 2016, 8 pages.
U.S. Appl. No. 15/416,986, filed Jan. 26, 2017, by Satish et al.
U.S. Appl. No. 15/594,017, filed May 12, 2017, by Satish et al.
Non-Final Office Action dated Feb. 21, 2019, for U.S. Appl. No. 15/594,017, filed May 12, 2017, 24 pages.
Notice of Allowance dated Jan. 24, 2019, U.S. Appl. No. 15/416,986, filed Jan. 26, 2017, 9 pages.

* cited by examiner

METHOD FOR ESTIMATING BLOOD COMPONENT QUANTITIES IN SURGICAL TEXTILES

CROSS-REFERENCE TO RELATED APPLICATIONS

This application claims priority to U.S. Provisional Patent Application 62/387,222, filed on Dec. 23, 2015. This application is also related to U.S. patent application Ser. No. 13/544,664, filed on Jul. 9, 2012, which is incorporated in its entirety by this reference in its entirety.

TECHNICAL FIELD

This invention relates generally to the field of blood loss management and more specifically to a new and useful method for estimating blood component quantities in surgical textiles in the field of blood loss management.

SUMMARY

This invention relates generally to the field of blood loss management and more specifically to a new and useful method for estimating blood component quantities in surgical textiles in the field of blood loss management. Systems and methods for detecting, counting and analyzing the blood content of a surgical textile are provided, utilizing an infrared or depth camera in conjunction with a color image.

In one example, a system for measuring blood content is provided, comprising a color imaging system configured to acquire color images, an infrared imaging system, to acquire infrared images, a processor configured to identify a surgical textile shape using the infrared images, generate shape information from the infrared images, use the shape information to identify surgical textile pixels in the color images, and extract blood information from the surgical textile pixels. The processor may be further configured to transform the infrared images to a coordinate system corresponding to the color images, to generate at a depth image from one of the infrared images, to identify a planar set of pixels in the depth image, and/or to detect a surgical textile image perimeter in the depth image. The detection of the surgical textile image perimeter may be performed by looking for a sharp vertical depth drop-off in the depth image. The processor may be further configured to downsample the depth image or the infrared image, to generate a mask image from the downsampled depth image, to upsample the mask image, to perform fill-in of missing infrared pixel region in the infrared images, to generate a mask image using the detected perimeter, and/or to transform the mask image to a coordinate system of the color images. The detected perimeter may be a top edge and a bottom edge of a surgical textile image, or may be opposing edges of a surgical textile image, and/or corners of a surgical textile image.

In another example, a method of analyzing an object containing a blood component is provided, comprising acquiring a depth image and a color image of an object containing a blood component, using the depth image to determine the presence of the object in a field of view, using the color image to estimate the a blood component characteristic. The method may further comprise generating an image mask using the depth image, and applying the image mask to the color image to eliminate background pixels. The method may further comprise applying at least one of erosion and dilation image processing to the depth image.

In still another example, a method for estimating a fluid component quantity in surgical textiles is provided, comprising capturing a first infrared image of a field of view at a first time, detecting a shape or surface characteristic of a surgical textile in the first infrared image, indexing a frame counter upon detecting the shape or surface characteristic in the first infrared image, capturing a second infrared image of the field of view at a second time succeeding the first time, detecting a surface characteristic of a surgical textile in the second infrared image, indexing the frame counter upon detecting the shape or surface characteristic in the second infrared image, and indexing a non-detection counter upon a failure to detect a shape or surface characteristic of a surgical textile in the second infrared image. The method may further comprise clearing the frame counter and the non-detection counter upon reaching a pre-specified value. The method may further comprise comparing the frame counter to a threshold value, capturing a color image of the field of view if the frame counter may be equal to or exceeds the threshold value, transforming a region of the color image corresponding to a surgical textile into an estimation of a blood component quantity, and clearing the frame counter. The method may further comprise generating an image mask using the second infrared image, and using the image mask with the color image to identify the region of the color image corresponding to the surgical textile.

In another example, a method of performing fluid monitoring is provided, comprising capturing an infrared image of a field of view, capturing a color image of the field of view, generating an image mask using the infrared image, and using the image mask with the color image to identify a region of the color image corresponding to a surgical textile. The method may further comprise transforming the infrared image to the geometry perspective of the color image. The method may further comprise downsampling the infrared image prior to generating the image mask. The method also may further comprise upsampling the image mask before using the image mask to identify the region of the color image.

DESCRIPTION OF THE EMBODIMENTS

Overestimation and underestimation of patient blood loss is a significant contributor to high operating and surgical costs for hospitals, clinics and other medical facilities. Specifically, overestimation of patient blood loss results in wasted transfusion-grade blood and higher operating costs for medical institutions and can lead to blood shortages. Underestimation of patient blood loss is a key contributor of delayed resuscitation and transfusion in the event of hemorrhage and has been associated with billions of dollars in avoidable patient infections, re-hospitalizations, and lawsuits annually. Thus, there is a need in the surgical field for a new and useful system and method for estimating extracorporeal blood volume in a physical sample.

The systems and methods described herein utilize a color camera system to acquire images of surgical textiles or other operating room surfaces and to estimate the blood content in each image. In addition, the system can also track the number of surgical textiles used during a procedure, to assist the surgical or procedure staff with confirming that all surgical textiles were accounted for, and not left in the patient, prior to surgical closure. The surgical textiles may include items such as an absorbent surgical gauze sponge, a surgical dressing, a surgical towel, surgical gown, scrubs or other clothing, a table, bed or bed sheet, wall, floor surface, an external skin surface, a surgical glove, a surgical implement, or any other surface, material, substrate, or object.

To facilitate the presentation of objects to the color camera system for assessment and/or counting, an infrared or other type of camera configured to provide depth information may be used to detect the presentation of the object for analysis. Depth information from such a system may more easily distinguish the object, which is located in the foreground, from other objects not intended to be analyzed, and will be located in the background. Examples of optical systems that can provide depth information include rangegated time-of-flight (ToF) cameras, RF-modulated ToF cameras, pulsed light ToF, and projected light stereo cameras, etc.

To improve the accuracy of the detection process, other features of the object may also be detected to reduce the risk of false positive results. The reliability of the detection process may also be improved by identifying the presence of the object in multiple consecutive frames before analyzing the object and presenting the results.

1. Applications

Figure 1:
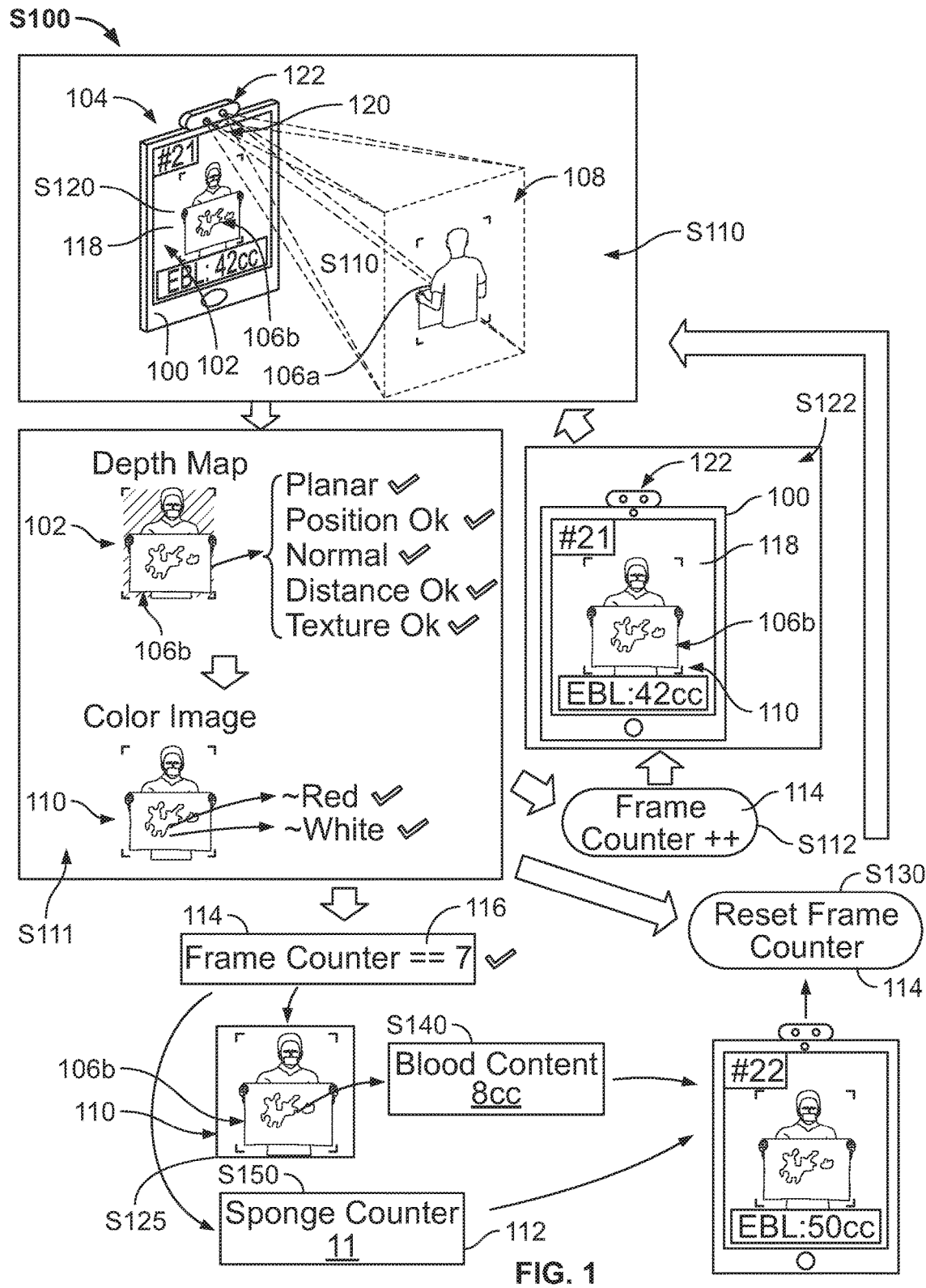
FIG. 1 is a flowchart representation of a method for analyzing a surgical textile.

Generally, as depicted in FIG. 1, the various methods described herein may be executed by a computing device 100 to acquire one or more images 102 using an optical sensor system 104 to detect a surgical textile 106a, such as a surgical gauze, a surgical sponge, or a surgical towel, in the field of view 108, as depicted in S110. In S111, the image 102 is analyzed to confirm the presence of the surgical textile (image) 106b over a sequence of frames output by the optical sensor system in S111, and to automatically capture a color image 110 of the surgical textile 106b in S125 once its presence is confirmed, or utilize the last color image concurrently captured with images 102. The computing device 100 can then index a local surgical textile counter 112 in S150, and in S140 locally transform color values of pixels in the color image 110 into an estimation of an amount of a blood component (e.g., a mass of hemoglobin, a volume of whole blood) in the surgical textile 106b, or pass the color image 110 to a remote computer system for such processing.

In particular, the computing device 100 may be configured to detect a possible surgical textile image 106 in a first frame (e.g., an infrared image) and to index a frame counter 114 according in Block S112, and to index the frame counter 114 again if a possible surgical textile 106 is again detected in the subsequent frame, or to clear the frame counter 114 in Block S130 if a surgical textile image 106b is not detected in the next frame. This process is repeated and the frame counter 114 is indexed for as a long as a possible surgical textile 106b is detected in subsequent frames and until the frame counter 114 contains a value equivalent to a threshold value 116. Once the frame counter contains a value equivalent to a threshold value 116, the computing device can record a color image 110 of the surgical textile 106 and process the color image 110 to determine its content of a blood component (e.g., hemoglobin) in Block S140 and/or to update a textile counter 112 for the detected surgical textile 106 in Block S150. For example, the computing device 100 can implement a threshold value 116 of "7," which correlates to seven consecutive frames containing a region determined to likely correspond to a surgical textile 106, and the computing device 100 can capture a digital color photographic image 110 of a surgical textile 106b once the frame counter 114 contains a value of "7" and process this image 110 to determine the mass or volume of hemoglobin or whole blood component in the surgical textile 106. In other examples, the threshold value may be set in the range of about 3 to about 100, or about 5 to about 70, or about 30 to about 50, or about 8 to about 20. By tracking a surgical textile 106 through a sequence of frames and only confirming the presence of the surgical textile 106b if the surgical textile 106b is detected in a minimum number of consecutive frames, the computing device 100 may minimize or eliminate false positive confirmations of surgical textiles 106b, thereby minimizing or eliminating erroneous textile counter events and automated collection and processing of images that do not contain surgical textiles. This tracking process may also improve computational efficiency, by reducing the need to perform blood content determination of every color image.

In further embodiments, the computing device 100 may also be configured to automatically detect a surgical textile 106a within its field of view 108 (i.e., within the field of view of one or more optical sensors of the optical sensor system 104 integrated into and/or connected to the computing device 100), thereby reducing or eliminating need for the user to manually trigger capture of a bloodied surgical textile, such as depression of a foot pedal, touch control, gesture control or voice control. Furthermore, the computer system 100 may be configured to provide real-time visual feedback though an integrated or connected display 118, such as a visual indicator that a surgical textile 106a is detected within the field of view 108 of the computing device 100, that an image of the surgical textile was captured, and/or a prompt to manipulate the surgical textile 106a to yield a sufficient or higher-quality image.

The methods described herein may be executed locally by the computing device 100 installed or arranged within an operating room, a delivery room, an ambulance, or in any other medical or emergency response space or unit. However, the method may also be executed locally and/or remotely, such as by a remote server. Blocks of the method are described herein as detecting surgical sponges and capturing and processing images of surgical sponges. However, Blocks of the method can additionally or alternatively be implemented to detect surgical gauzes, surgical towels, or any other textile and to capturing and processing images of such textiles.

2. Exemplary Methods

As shown in FIG. 1, a general method S100 for estimating blood component quantities in surgical textiles comprises, at a first time point, using the optical system 104 to capture a first infrared or depth image 102 of a field of view 108 in Block S110. In this particular example, the optical system 104 comprises a computing device 100 with a built-in display 118 and a color camera or color imaging system 120 on the same side of the computing device display 118, but in other examples the computing device 100 may be configured to use a camera on the opposite side of the display 118. To capture the depth image 102, an infrared camera or depth imaging system 122 is directly mounted on the computing device 100, but in other examples the depth imaging system 122 may be mounted at a location spaced apart from the computing device 100. In some variations, the infrared or depth camera 120 is configured to be mounted to a specific computing device 100 such that the optical axis of this second camera 121 is aligned vertically and parallel to the optical axis of the color camera 120. In other examples, however, the optical axis of the second camera 121 may be aligned with the horizontal axis of the color camera 120, or may not be aligned with either axis of the color camera. The second camera 122 may alternatively be configured to intersect the optical axis of the color camera 120 at a location that is at a distance in the range of about 15 cm to 200 cm, or about 30 cm to about 100 cm, from the color camera 120.

The image 102 is then analyzed at S111 to detect a surface or shape characteristic corresponding to a surgical textile 106b in the first infrared image 102. If the presence of a surgical textile 106b is confirmed, a frame counter 114 is indexed in S112. At a second or subsequent time point succeeding the first time point, a second or subsequent infrared image 102 of the field of view 108 is captured, and in response to detecting a surface or shape characteristic of a surgical textile 106b in the second or subsequent infrared image 102, indexing the frame counter 114 again. This detection is performed repeatedly until either a threshold value 116 is reached, or in response to failure to detect a surface or shape characteristic of a surgical textile in the second or a subsequent infrared image, clearing the frame counter in S130. Upon the frame counter containing a value equivalent to a threshold value at S113, a color image 110 of the field of view 108 may be captured by the color camera 120. In variations wherein color images are taken with the infrared or depth images 102, the last color image 110 from those taken during Block S110 or S111 may be used. The regions of the color image 110 corresponding to the surgical textile 106b are identified, and then those regions are further analyzed to identify the portions containing blood. Those portions are then transformed into an estimation of a blood component quantity in Block S140. The system then clears the frame counter in S130.

Further variations of the method are also depicted in FIG. 1. For example, at a first time point, when a first image 102 of a field of view 100 is captured by the optical system 104 in S110, and a rendered form of the first image 102 may be provided on a display 118 in S120. This displayed image 102 may correspond to a depth image or a color image. In response to detecting a first surface or shape characteristic of a surgical textile 106b in the first image 102, a frame counter 114 is indexed in S112 and, on the display 118, highlighting a region of the first image 102 corresponding to the first surface or shape of the surgical textile 106b in Block S122. This variation of the method may also include, at a second or subsequent time point succeeding the first time point, capturing a second or subsequent image 102 of the field of view 108, rendering a form of the second or subsequent image 102 on the display 118; and, in response to detecting a second surface or shape characteristic of a surgical textile 106b in the second image 102, indexing the frame counter 114 at S112 and, on the display 118, highlighting a region of the second image 102 corresponding to the second surface or shape based on a value of the frame counter 114 at S122. Upon a failure to detect a second surface or shape characteristic of a surgical textile 106b in the second or subsequent image 102, the frame counter 114 is cleared in S130, or in response to the frame counter 114 containing a value equivalent to a threshold value 116, indexing a textile counter 112 in Block S150 and clearing the frame counter 114. In procedures or surgeries utilizing different surgical textiles, multiple surgical textile counters may be provided, and the counter for the corresponding surgical textile 106 may be indexed in S150.

3. System

As shown in FIG. 1, the computing device 100 includes an imaging system 104 defining a field of view 108 and configured to capture depth and color data from its field of view 108. In particular, the computing device 100 can include a depth imaging camera or system 122 that outputs depth information or maps 102 of the field of view 108 and a color imaging camera or system 120 that outputs color images 110 of the field of view 108.

Figure 3:
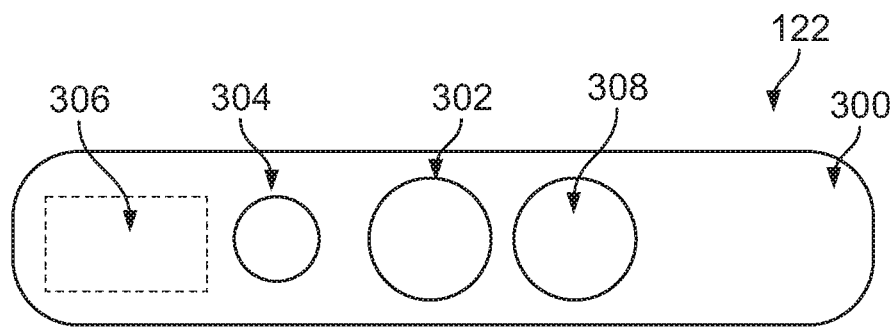
FIG. 3 is a schematic representation of an exemplary depth imaging system.
Figure 4:
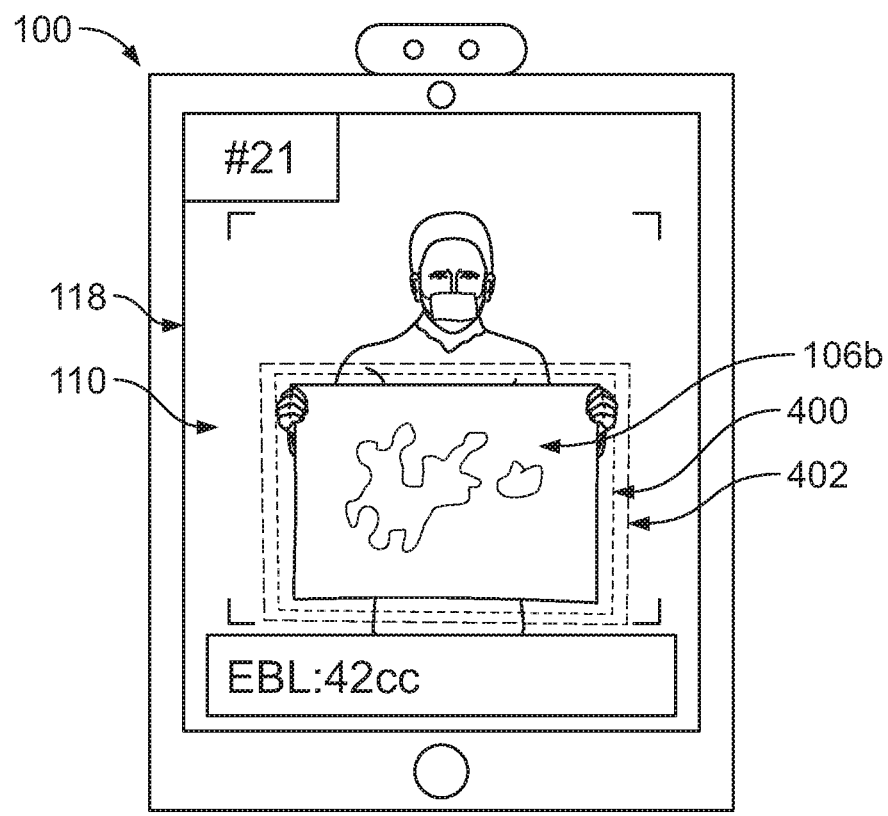
FIG. 4 depicts an exemplary computing device and user display, highlighting the surgical textile.

As show in FIG. 3, in one implementation, the depth imaging system 122 includes a housing 300 with a structured light infrared ("IR") projector 302 that defines a projection field of view and projects infrared light in a pattern of dots into projection field of view, an IR camera 304 that defines an infrared field of view substantially similar to the projection field of view and configured to capture a sequence of infrared images (or "infrared frames") of the infrared field of view; and an internal processor 306 configured to transform a distorted dot pattern detected by the IR camera 304 recorded in each infrared image into a depth map 102, such as based on the density or displacement of dots across each infrared image. The IR projector may comprise an IR laser or diode. U.S. Pat. No. 8,374,397, which is incorporated by reference in its entirety, is one example of this IR depth technology. Therefore, during operation of the computing device 100, the depth imaging system can output a sequence of depth maps 102, wherein each depth map 102 contains a representation of distances between the IR camera 122 and surfaces within the infrared field of view at a corresponding time. Of course, other depth cameras besides IR based cameras may also be used, including but not limited to other types of structured like cameras, stereoscopic cameras where stereo triangulation may be used on the stereoscopic image pairs to determine distance, depth of focus cameras, and other known types of depth cameras. In some variations, the depth imaging system 122 may include a color camera system 308 which may be used instead of internal color camera system of the computing device.

The color imaging system may include a color camera 120, such as a CCD or CMOS camera supporting red, green, and blue color channels. The color camera 120 may also define a color field of view that is substantially similar to (i.e., substantially overlaps) the infrared field of view of the IR camera 122 (and therefore the projection field of view). As described below, the computing device 100 can trigger or activate the depth imaging system 122 and the color imaging system 120 to generate a depth map 102 and to capture a color image 110, respectively, during each sampling period during executing of the method, such as at a rate of 30 Hz. In other examples, the sampling rate of the camera(s) may be in the range of about 0.1 Hz to about 1 kHz, or about 60 Hz to about 240 Hz. The computing device 100 can thus capture one depth map 102 and one color image 110 (a "frame pair") during each sampling period and process both depth and color data for each sampling period to detect the presence of a surgical sponge or other surgical textile 106 in the field of view of the computing device 100 at the corresponding time. Alternatively, the computing device 100 can sample the depth imaging system and process depth map data to detect surgical sponges or surgical textiles in the field of view 108 of the computing device 100, and the computer system 100 can capture a color image 110 through the color imaging system once a value in the frame counter 114 reaches a threshold value 116, as described below. In still other embodiments, the ratio of the depth images 102 to color images 110 may be fixed or pre-determined, and in the range of about 3:2 to about 100:1, or about 2:1 to about 50:1, or about 30:1 to about 50:1.

The computing device 100 may also include a display 118 adjacent the IR and color camera 122, 120. The display 118 can define a viewing area substantially normal to the fields of view of the IR and color cameras such that a user (e.g., a nurse, a technician, an anesthesiologist) holding a surgical sponge can stand in front of the IR and color cameras 122, 120 while viewing content on the display 118. For example, as described below, the display 118 can render any one or more of a) an indicator that the sponge was detected, b) an indicator that an image of the sponge was recorded, c) a value on the sponge counter; and d) a prompt to manipulate the sponge before an image is captured, etc. substantially in real-time. In one example, the computing device includes: a tablet computer including a forward-facing color camera and an integrated display; and an IR projector and IR camera mounted to the tablet, facing outwardly from the tablet, and defining projection and infrared fields of view substantially similar to the color field of view of the color camera. However, the computing device can include any other integrated or connect optical, imaging, and/or processing components arranged in any other suitable way.

4. Exemplary User Experience

In one example, the computing device 100 is installed in an operating room and executes the method depicted in FIG. 1, in the form of a native blood loss monitoring application utilized during an operation, surgery or procedure. In this example, the computing device 100 continually captures infrared 102 and/or color images 110 of its field of view 108 and discards these images if no surgical sponge 106a is detected in the images or frames. The computing device 100 may also renders these frames or images on the display 118 substantially in real-time. The rendered images are typically the color images 110, but may also be the depth image 102 or a composite image of the color and depth images. During the operation, a user (e.g., a nurse, a technician, an anesthesiologist) may hold a surgical sponge 106a in front of the imaging system 104. With the surgical sponge 106a now in the field of the view 108 of the imaging system 104, the imaging system 104 captures a first depth map 102 and/or a first color image 110 (a "first frame pair" or "frame set" if more than two grouped images or maps) during a first sampling period following the presence of the surgical sponge 106a in the field of view 108 of the computing device 100 in S110. The computing device 100 then implements machine vision techniques described herein to correlate a region of the first depth map 102 (and a corresponding region of the first color image 110) with a surgical sponge 106a and indexes a frame counter 114 from "0" to "1" in S112. In response to detecting the surgical sponge image 106b in the first depth map 102 (or in the first color image 110), the computing device 100 renders the first infrared image 102 (or the first color image 110) on the display 118 with a colored (e.g., green, red, yellow or other distinctive color) line or shape overlay 400 of a first width along the perimeter of the detected surgical sponge and/or a colored overlay area of a first opacity over the detected area of the surgical sponge.

In the succeeding sampling period, the imaging system 104 captures a second depth map 102 and/or a second color image 110 (a "second frame pair" or "second frame set"), and the computing device 100 again implements machine vision techniques to correlate a region of the second depth map 102 (and a corresponding region of the first color image 110) with the surgical sponge 106a and indexes the frame counter 114 from "1" to "2." In response to detecting the surgical sponge image 106b in the second frame pair, the computing device 100 renders the second infrared image 102 on the display with a broader colored line or shape overlay of a second width or line length 402—greater or different than the first width or line length—along the perimeter of the detected surgical sponge 106b and/or a colored overlay area of a second opacity—greater or different than the first opacity—over the detected area of the surgical sponge 106b.

The computing device 100 can repeat this process to capture frame pairs during subsequent sampling periods, to detect surgical sponges 106b in the frame pairs, to index the frame counter 114 accordingly, and to refresh the display 118 with a current depth map 102 (or color image 110) with overlay perimeter and/or overlay area of line width 400, 402 and opacity, respectively, representative of the frame counter value. To dynamically demonstrate the process of confirming the presence of the surgical textile 106b in the images 102, 110, increasing greater widths of overlays or other changing indicia may be provided. For example, the color of the overlay may also change from red to yellow to green. Once the value on the frame counter 114 reaches a threshold value, (e.g., "7"), the computing device captures a color image through the color camera, renders a visual indicator that the color image was captured on the display, and resets the frame counter to "0" without additional manual input. For example, for the imaging system operating at 30 Hz and for a preset threshold value of "7" set for the frame counter, the computing device can perform the forgoing methods and techniques to detect, confirm, and capture an image of a surgical sponge in less than 0.3 second from entry of the surgical sponge into the field of view of the computing device. In other examples, the threshold value may be set in the range of about 5 to 100, or about 5 to 50, or about 4 to about 30, or about 20 to about 40. The computing device may also be further configured to perform the analysis for the removal of the surgical textile 106a from the field of view 108 as described in S500 and FIG. 5.

The computing device 100 may be configured to perform the methods and techniques described in U.S. patent application Ser. No. 13/544,664 to transform color values of pixels in the image into an estimation of blood component quantity in the imaged surgical sponge in Block S140. In response to confirmation of the surgical sponge 106b in the field of view 108 of the computing device 100 and capture of the color image 110 of the surgical sponge 106a, the computing device 100 may also index a sponge or surgical textile counter 112 in Block S150 in order to maintain a total count of surgical sponges passing the computing device 100 during the operation or procedure.

5. Classifier

Block S110 of the method recites, at a first time point, capturing a first image 102 of a field of view 108. Generally, during each sampling period, the computing device 100 functions to capture an infrared image 102 and/or a color image 110 through the imaging system 104 in S110. As described above, the computing device 100 may also transforms the infrared image 102 into, or to extract therefrom, a depth map of its field of the view. The computing device 100 can repeat this process over time during its operation, such as at a sampling rate (or "frame rate") of 30 Hz, or other sampling rate as described herein. However, the computing device can capture depth and color data of its field of view at any other sampling rate in any other way and through any other suitable type of sensor in Block S110.

Figure 2:
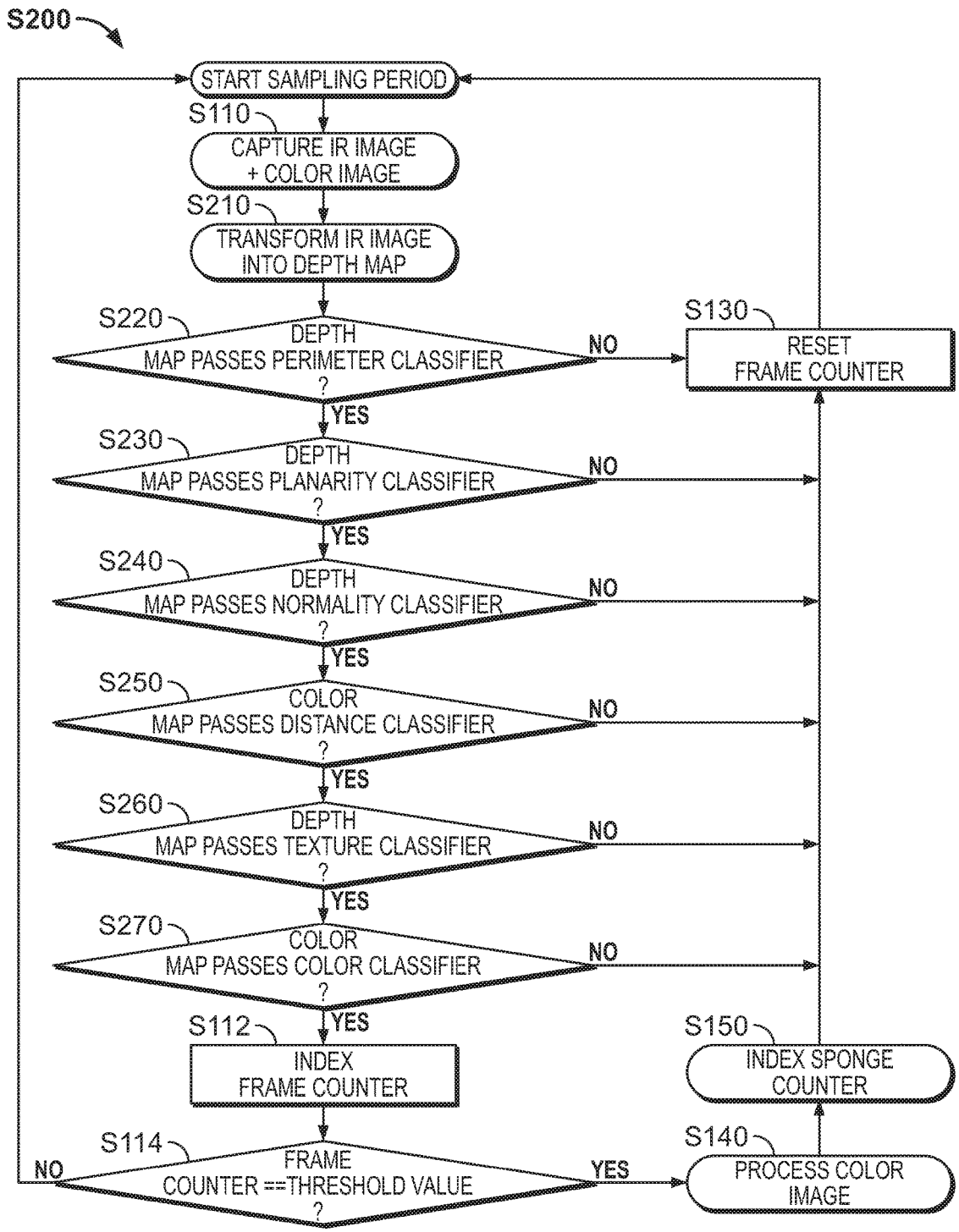
FIG. 2 is a flowchart representation of one variation of the method for classifying and counting a surgical textile for certain characteristics.

After acquiring the image(s) 102 and/or 110, in S111 the computing device 100 analyzes the image(s) 102 and/or 110 to determine the presence of one or more image characteristics therein, or to otherwise classify the image(s) 102 and/or 110 captured in the current sampling period as either containing a sponge or surgical textile 106b, or not containing a sponge or surgical textile 106b. Based upon this determination, the computing device 100 may then index the frame counter in S112, or clear the frame counter in S130, respectively. In particular, the computing device 100 can apply one or more classifiers to a depth map 102 and/or a color image 110 captured during a sampling period to determine if a surgical sponge or textile 106a is present or is not present in the field of view 108 of the computing device 100 during the sampling period and to manipulate the frame counter 114 accordingly, as shown in FIGS. 1 and 2.

In one exemplary method S200, the computing device 100 captures an IR and/or color image 102, 110 as in S110 of FIG. 1, and then optionally transforms image 102 and/or 110 into a depth map in S210. In some examples, transformation may not be needed, as the IR "image" that is output from the IR imaging system 122 is a depth map, or the depth map may be extracted from the alpha channel (or other channel) of the infrared image, without any transformation or calculation needed. In S220, the computing device 100 applies a perimeter classifier to the depth map captured during a sampling period to correlate an area in the depth map with a possible surgical sponge. In one example, to compensate for a surgical sponge that may not be held in a position substantially normal to the infrared camera, the computing device can scan the depth map—along both an X-axis and a Y-axis of the depth amp—to identify changes in depth along the Z-axis in the depth map exceeding a threshold of 10% or more, 20% or more, 30% or more, or 40% or more, across a line of 10 contiguous pixels. In this example, the computing device 100 can correlate each short, contiguous line of pixels across which a depth value exceeds 10% with an edge condition and then assemble adjacent and similar edge conditions within the depth map into perimeters of discrete surfaces within the field of view of the computing device. Once these discrete surfaces are thus detected, the computing device can implement template matching, surface mesh, or other machine vision techniques to identify a discrete, approximately rectilinear surface within the depth map with a possible surgical sponge. The computing device may thus scan the depth map for an area bounded by an approximately rectilinear perimeter characterized by a sharp increase in depth (from the imaging system) from the interior of the area to the exterior the area. In this implementation, the computing device may implement a geometry classifier that compensates for compliance (e.g., non-rigidity) of surgical sponges, including curvature of one or more sides of a rectilinear sponge when held vertically in front of the imaging system, which may vary with volume of fluid in the surgical sponge, tension applied to the surgical sponge by the user, etc.

In the foregoing implementation, the computing device may also reject all detected surfaces not coincident a predefined point or region in the depth map, such as all surfaces not containing the single pixel or small pixel cluster at the lateral and longitudinal center of the depth image. The computing device may thus apply a 2D position classifier to the depth map to reject surfaces not substantially centered in the field of view of the imaging system. However, the computing device may implement any other geometry classifier in any other way to detect an approximately rectilinear perimeter of a contiguous surface in the depth map and to correlate this surface with a possible surgical sponge.

In other examples, the perimeter detection may be set to identify more abrupt changes or decreases in the depth, e.g. more than 15%, 20%, 30%, 40%, 50%, 60% or 70%, for example. Although the perimeter detection may be performed for all four edges of a square or rectangular surgical textile, in other examples, the computing device 100 may only perform edge scanning to the X-axis or Y-axis for depth changes, but not the other axis, and then extrapolate the edges along the other axis by connecting the end points of the edges with an extrapolated edge. Thus, in some variations, only the top and bottom edges may be detected and the lateral edges may be extrapolated from the ends of the top and bottom edges. Alternatively, the lateral edges may be detected and the top and bottom edges are extrapolated.

In another implementation, the computing device 100 applies in S230 an optional planarity classifier to a selected surface in the depth map—correlated with a possible surgical sponge or textile, as described above—to determine or confirm that the selected surface is sufficiently planar to indicate a surgical sponge or textile 106a. In this implementation, the computing device 100 can select a set of pixels (e.g., three, four, five, six, or ten) in the depth map, map a virtual plane to the set of pixels, and then calculate a histogram of normal distances from the virtual plane to other pixels within the depth map corresponding to the selected surface. Thus, if the histogram indicates that the selected surface remains within a threshold distance of the virtual plane across its height and width (with optional removal of outliers to reduce skewing), the computing device 100 can determine or assess whether the selected surface is of sufficient planarity to indicate a surgical sponge held from its upper corners. However, if the histogram indicates that regions of the selected surface breach a threshold distance from the virtual plane, the computing device 100 can discard the selected surface as not corresponding to a surgical sponge held from its upper corners. In this implementation, the computing device can implement a threshold distance that compensates for folds, creases, and/or ripples in a surgical sponge, such as a threshold distance of ±0.1", ±0.25", ±0.5", ±0.75", or ±1". In this implementation, if the selected surface is rejected under the planarity classifier, the computing device can generate a textual and/or graphical prompt to stretch the surgical sponge in order to pass the planarity classifier, and the computing device can render this prompt on the display substantially in real-time.

Figure 6:
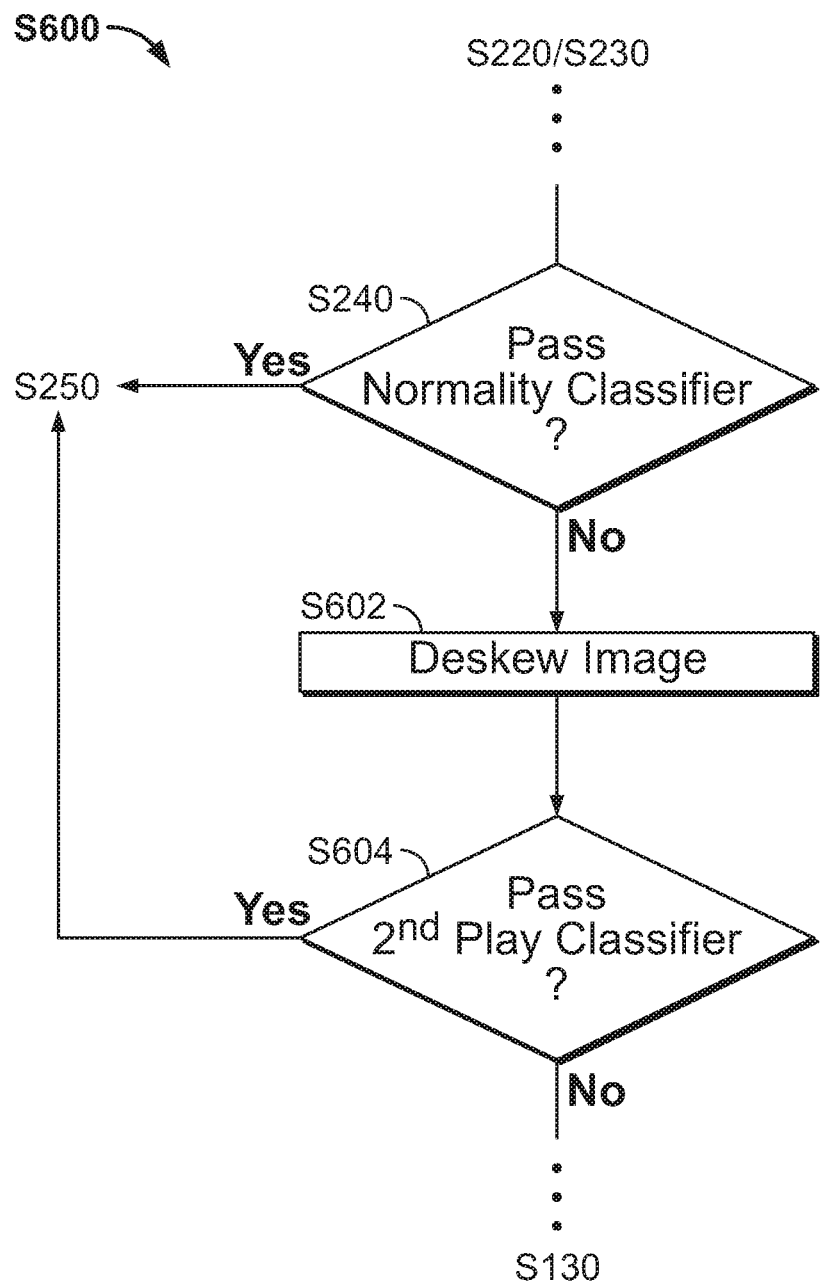
FIG. 6 is a flowchart representation of a method of de-skewing and reassessing an image.

In yet another implementation, the computing device applies a normality classifier in S240 to the depth map to confirm that the selected surface is sufficiently normal to the field of view of the imaging system to qualify for imaging and processing in Block S140 of FIG. 1. For example, the computing device 100 can calculate a virtual ray normal to the virtual plane described above, reject the selected surface if the virtual ray forms a maximum angle to a center of the field of view of the imaging system that exceeds a threshold angle, and pass the selected surface if the maximum angle formed between the virtual ray and the field of view of the imaging system remains within the threshold angle. In alternate method S600, depicted in FIG. 6, after applying the normality classifier S240, instead of the rejecting images that are not sufficiently normal to the computing device 100 or optical system 104, the computing device 100 may computationally deskew or dewarp the depth map in S602. To dewarp the depth map, the computing device 100 may detect the four corners and/or four edges of the surgical textile 106b in the image 102, and apply a 3D rotational or translational matrix to normalize the corners or edges to the same plane in the Z-axis.

After dewarping, the computing device 100 may reapply a planarity classifier to the dewarped surgical textile 106b, and then either reject the selected surface if the maximum variation in distance values for pixels across the selected surface in the dewarped depth image exceeds a threshold distance, accounting for folds, creases, and/or ripples in a surgical sponge, or pass the selected surface if the maximum variation in distance values for pixels across the selected surface in the dewarped depth image remains within the threshold distance, to continue further classification and/or processing using the dewarped depth image. The threshold distance may be in the range of about −1 cm to about +1 cm, about −2 cm to about +2 cm, or about −3 cm to about +3 cm, or about −4 cm to about +4 cm. If the dewarped image fails the planarity classifier S604 after dewarping in S602, the computing system 100 may then reset the frame counter in S130 with or without providing an indicia or message on the display 118 of the computing device 100 to attempt to reposition the surgical textile 106a in the field of view 108 in a relatively more normal orientation. Alternatively, if the selected surface is rejected under the normality classifier, the computing device may generate a textual and/or graphical prompt in order to adjust the surgical sponge to pass the normality classifier for an additional specified number of frames, and the computing device can render this prompt on the display substantially in real-time. The number of frames may be in the range of about 15 frames to 120 frames, or about 30 frames to about 60 frames, for example.

Referring back to method S200 in FIG. 2, the computing device may optionally apply a distance classifier S250 to the depth map to confirm that the selected surface is within a proper depth of the imaging system 104. For example, once the computing device 100 determines that the selected surface is sufficiently planar and sufficiently normal to the field of view of the imaging system in S230 and S240, respectively, the computing device 100 may reject the selected surface if more than a minimum number (e.g., 1%) of pixels in the depth image 102 representing the selected surface of the surgical textile 106b fall outside of a preset depth range (e.g., 0.5 meter to 1.25 meters, or 30 cm to about 100 cm, or about 40 cm to about 75 cm) from the imaging system 104. In this implementation, if the selected surface is rejected under the distance classifier at S250, the computing device 100 may optionally generate a textual and/or graphical prompt on the display 118 to move the surgical sponge 106a closer or farther from the optical system 104 of the computing device 100, in a further attempt to pass the distance classifier S250. The computing device 100 can render this prompt on the display 118 substantially in real-time.

In the foregoing implementation, the computing device 100 may also transform a pixel length and a pixel width of the selected surface in the depth image into a real length and a real distance based on distance values of pixels in the depth image. The computing device may then reject the selected surface if either the real length or the real width of the selected surface falls outside of a preset length range or a preset width range, respectively, or to confirm that such surgical textiles are being used. The preset dimensions for the surgical textiles may include 2"×2", 3"×3", 4"×4", 4"×8", 4"×12", 4"×16", 4"×18", 12"×12", 16"×16", 16"×24", 18"×30", 15"×24", 16"×23", 12"×13", 13"×18", 24"×24", 36"×8", 36"×36" and the like. For each sponge type, a user may enter the sponge type and/or size at the start of the surgery or procedure, and computing device 100 may be configured to detect the dimensions of those surgical textiles within 0.5" or 0.75" along a width or length for dimensions less than 5", 8" or 10", and 0.5", 1", 1.5" or 2" for dimensions in greater than 8", 10", 12" or 15", for example.

In another implementation, the computing device applies a texture classifier at S260 to the depth map in order to determine if the real texture of the selected surface represented in the depth map corresponds sufficiently to a surgical textile. In one example, the computing device 100 may be configured to project or define pixel clusters (e.g., 25-pixel by 25-pixel clusters) in the depth map—corresponding to the selected surface—onto a virtual plane and then apply machine vision texture analysis methods and techniques to quantify the texture of the normalized region of the depth map corresponding to the selected surface. Thus, if the quantitative value of the texture of the selected surface falls within a single value range or multiple distance value ranges representative of dry surgical sponges, damp surgical sponges, and saturated surgical sponges, the computing device can accept the selected surface. Otherwise, the computing device can reject the selected surface. In other examples, a Fast Fourier Transformation or wavelet transformation may be applied to the textile 106b in the image(s) 102, 110, to evaluate the frequency domain of the textile in one or more image channels, e.g. a RGB or depth channel. In some variations, if the detected texture characteristic matches a surgical textile in the library of the computing device 100 but does not match the surgical textile(s) selected by the user at the start of the surgery or procedure, the computing device 100 may prompt the user to confirm whether a new or different surgical textile should be indicated as being used, and may prompt the initialization or activation of a different surgical textile counter for that surgical textile.

In another implementation, the computing device 100 applies a color classifier S270 to the color image 110 in order to confirm that the selected surface contains one or more colors representative of a dry or bloodied surgical sponge. In one example, the computing device 100 accepts the selected surface if at least a threshold proportion (e.g., 70%) of pixels within a region of the color image corresponding to the selected surface contain a color within either a range of red values (e.g., [ff 00 00] to [ff 40 00]) or a range of near-white values (e.g., around [ff ff ff]), as shown in FIG. 1. Otherwise, the computing device can reject the selected surface.

However, the computing device 100 may also apply any other classifier parameter to the frame pair and/or to one or more selected surfaces within the depth map or color image in each frame pair. During operation, the computing device 100 may thus apply one or more classifier parameters to a current frame pair and can confirm a selected surface within the frame pair as representative of a surgical sponge if all applied classifier parameters pass the selected surface or pass the selected surface with sufficient confidence. Alternatively, the computing device 100 can confirm a selected surface within the frame pair as representative of a surgical sponge if at least a threshold number of applied classifier parameters pass the selected surface or at least a threshold confidence is reached by summing the results of all applied classifier parameters. The computing device can thus index the frame counter in Block S112, such as from "0" to "1" or from "4" to "5". In some further variations, the user may adjust the sensitivity and/or specificity of the computing device 100 via the user interface by adjusting the number or weight of classifiers that are applied or which are required to pass an image pair or image set.

Otherwise, if the foregoing conditions are not met, the computing device 100 may discard the frame pair as not containing an area representative of a surgical sponge 106b and reset the frame counter 114 to "0" in Block S130. The computing device 100 may also discard the frame pair and reset the frame counter to "0" if the surface selected in the current frame pair differs significantly in position, size, texture, depth, etc. from the surface selected in the preceding frame pair. For example, even if a surface possibly indicative of a surgical sponge is detected in a current frame pair, the computing device can reject the current frame pair and reset the frame counter if the center of the selected surface in the current frame pair is offset from the center of a selected surface in the preceding frame pair by more than 0.5" in any dimension. The computing device can thus reject surgical sponges and other surfaces moving through the field of view of the imaging system and only confirm any image sponge samples that are held substantially static within the field of view of the imaging system.

Although the classifiers S230, S240, S250, S260, S270 are depicted in S200 performed in a particular order, one of skill in the art will understand that a different order of these and other classifiers may be used, or that one more classifiers may be performed in parallel, such as in a multi-core and/or multi-threaded processor of the computing device 100.

6. Sponge Confirmation

Subsequently, in response to the frame counter 114 containing a value equivalent to a threshold value 116, the computing device records a color image 110 of the field of view 108 and clears the frame counter 114 in Block S130, either before or after further processing of the image 110 to estimate the blood content. Generally, for each frame pair in a sequence of frame pairs, the computing device 100 analyzes a frame pair independently of the preceding frame pairs to identify a surgical sponge or textile 106b in a frame pair or to confirm that a surgical sponge or textile 106b is not present in the frame pair and indexes or clears the frame counter accordingly, as shown in FIGS. 1 and 2. When the frame counter 114 contains a value equivalent to the threshold value 116, a total number of contiguous frame pairs equivalent to the threshold value have been determined to include a surgical sponge, or textile 106b and the computing device 100 may then confirm that a surgical sponge or textile 106a exists in the field of view 108 of the imaging system 104 and that its area in the field of view is known to a suitable degree of confidence once the frame counter 114 contains a value equivalent to the threshold value 116.

The computing device can implement a static, preset threshold value, such as one of "7," "10," or "15" or otherwise be in the range of about 5 to 100, or about 10 to 70, or about 30 to 50. Alternatively, the computer system can implement a custom threshold value set by the user. For example, the user can decrease the threshold value in order to reduce a time confirm and process an image of a surgical sponge, the user can increase the threshold value in order to reduce false positive detections of surgical sponges in the field of view of the imaging system. In still other variations, the computing device may comprise a discontinuity counter that during a surgery or procedure, for each instance where a certain minimum number of continuous frames is met, but where threshold number of frames is not met. Depending on the value of the discontinuity counter over time, the computing device may adjust the threshold value up or down, to alter the sensitivity of the detection method, which may accommodate location lighting or other environmental conditions that may affect the accuracy of the method S100.

Once the computing device thus confirms the presence of a surgical sponge 106a in its field of view 108, the computing device 100 may record a last depth map 102 and/or color image 110 captured by the imaging system, or may trigger the imaging system to capture a new depth map 102 and/or color image 110. The computing device 100 may then process this image pair, as described below.

Figure 5:
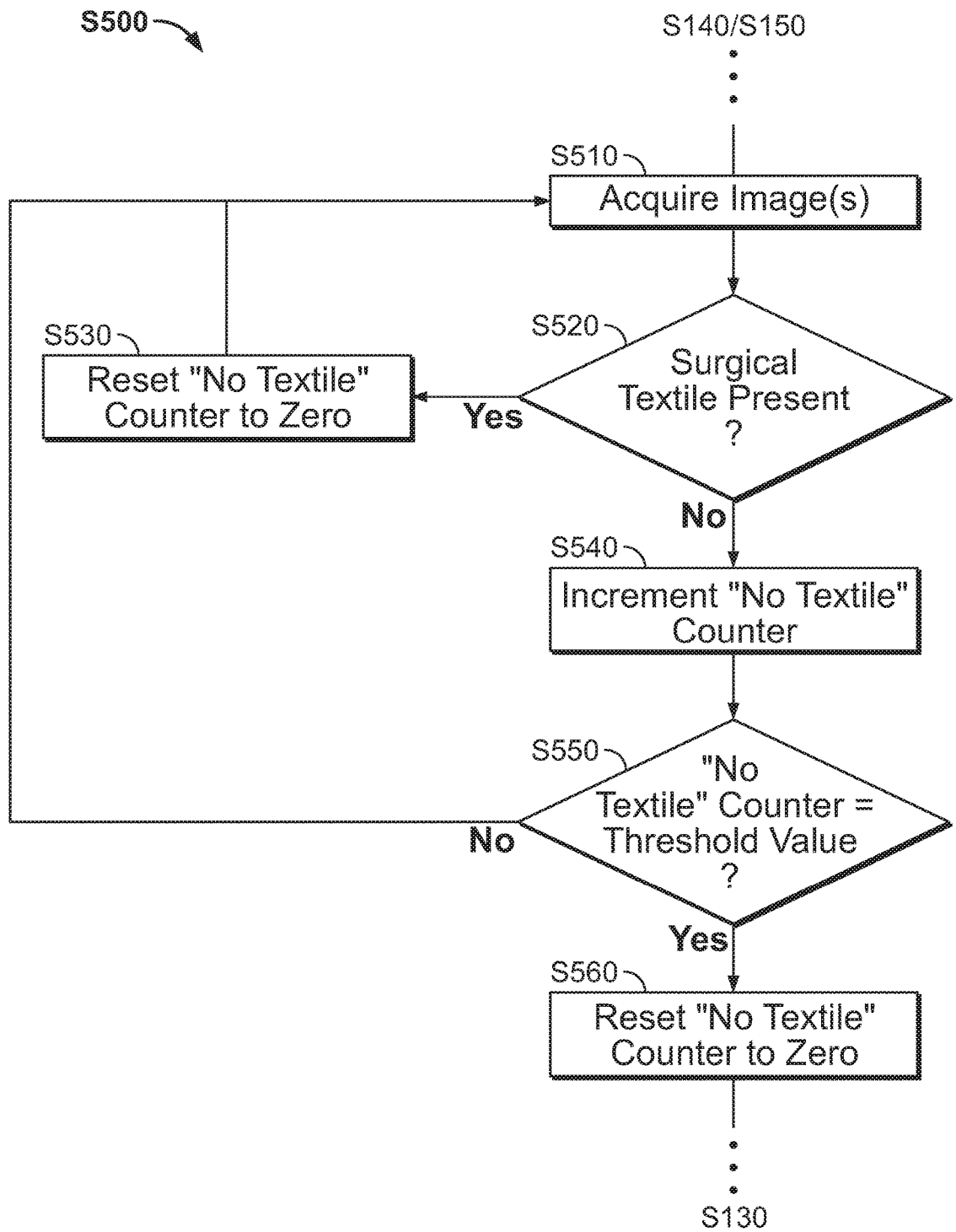
FIG. 5 is a flowchart representation of a method of detecting removal of a surgical textile from the field of view.

In some variations, to reduce the risk of inadvertently recounting or re-analyze the surgical textile 106a that was just presented to the optical system 104, before resetting the frame counter 114 in S130 or before reinitiating scanning for a new surgical textile 106a in S110, the computing device may be further configured to detect that the surgical textile 106a has been removed from the field of view 108, before acquiring images to identify the next surgical textile 106a, as shown in S500 of FIG. 5. After determining the estimated blood content S140 and/or incrementing the textile counter 112 in S150, in S510 the computing device 100 may acquire a new depth map 102 and/or color image 110 and determine in S520 whether the surgical sponge 106a has been removed from the field of view 108, or has otherwise not been detected in the image 102 or 110. If a surgical textile 106b is still present in the image 102 or 110, the user has not yet removed the prior surgical textile, or has not yet removed the surgical textile for a sufficient number of images or frames, and the computing device resets the "no textile" counter to zero.

If no surgical textile 106b is identified in the frame or image, in S540 the "no textile" counter is incremented and then the counter is checked against a "no textile" threshold value to determine whether a sufficient number of consecutive "no textile" frames or images have been identified. If the threshold value has been met, the "no textile" counter may be reset and the computing device may then reset the frame counter S130. In some examples, the "no textile" threshold value may be in the range of about 5 to 100, or about 5 to 50, or about 4 to about 30, or about 20 to about 40. The "no textile" threshold value in S500 may be the same or may be different from the threshold value 116 in S100 of FIG. 1.

7. Dynamic Classifier

In one implementation, the computer system applies the same ordered set of classifier parameters to each frame pair captured throughout its operation. Alternatively, the computer system can apply a set of classifier parameters to a frame pair based on a current value in the frame counter. For example, the computing device 100 may apply a perimeter classifier and a lateral/longitudinal position classifier to a frame pair when the frame counter contains a value of "0", and then apply a perimeter classifier and a normality classifier to a frame pair when the frame counter contains a value of "1". The perimeter classifier and the distance classifier may be applied to a frame pair when the frame counter contains a value of "2" or more, the perimeter classifier and a texture classifier may be applied to a frame pair when the frame counter contains a value of "6", the perimeter classifier and a color classifier may be applied to a frame pair when the frame counter contains a value of "7". However, the computing device can apply any other single or combination of classifier parameters to a frame pair to identify a surgical sponge in the frame pair or to discard the frame pair. In some other variations, the perimeter and/or position classifier may be applied to every frame, while the remaining classifiers are applied at different frames. In some variations, the different frames for the remaining classifiers are pre-determined, while in other variations, the different frames may depend on the processing time or completion of previous classifiers.

8. User Interface

Block S120 of the method recites rendering a form of the first image on a display, and Block S122 of the method recites, on the display, highlighting a region of the first image corresponding to the first surface. Generally, the computing device renders a form of the depth map (or the color image) from a current frame pair (i.e., a frame pair most-recently captured by the imaging system) on the display in Block S120 and renders a virtual overlay over the depth map in Block S122 to visually indicate that a surface possibly corresponding to a surgical sponge was detected in the frame pair as shown in FIG. 1.

In one implementation, the computing device dewarps depth maps and renders these dewarped depth maps on the display substantially in real-time. As each depth map is processed, as described above, the computing device can identify a region (e.g., a bounded area) with a depth map that may correspond to a surgical sponge and then render a visual indicator of this possible surgical sponge over the corresponding depth map on the display substantially in real-time. For example, the computing device can overlay a colored outline over the perimeter of the possible surgical sponge in the depth map rendered on the display. In this example, the computing device can set a line width of the outline proportional to the current value on the frame counter. Similarly, the computing device can set a color of the outline based on the current value on the frame counter, such as red when the current value on the frame counter is "0," orange when the current value on the frame counter is "2," yellow when the current value on the frame counter is "4," and green when the current value on the frame counter is "6." In another example, the computing device can overlay a translucent colored area overlay across a region of the depth map—rendered on the display—corresponding to the possible surgical sponge. In this example, the computing device can set an opacity of the area overlay proportional to the current value on the frame counter, such as 12% opacity when the current value on the frame counter is "0," 24% opacity when the current value on the frame counter is "1," 36% opacity when the current value on the frame counter is "3," . . . and 84% opacity when the current value on the frame counter is "7." Similarly, the computing device can set a color of the area overlay based on the current value on the frame counter, such as described above.

Therefore, in Blocks S120 and S122, the computing device can provide real-time visual feedback regarding detecting of a surgical sponge in the field of view of the imaging system. The computing device can additionally or alternatively implement any of the foregoing methods and techniques to render color images and/or overlays on the display substantially in real-time to provide such feedback to a user.

9. Mask

Once the presence of a surgical sponge or textile 106b is thus confirmed in the image 102 and/or 110, the computing device 100 may apply an image mask or impose a perimeter of a selected and confirmed area in the depth map onto the corresponding color image in the same frame pair to select a region of the color image to process in Block S140 and/or Block S150.

Figure 7:
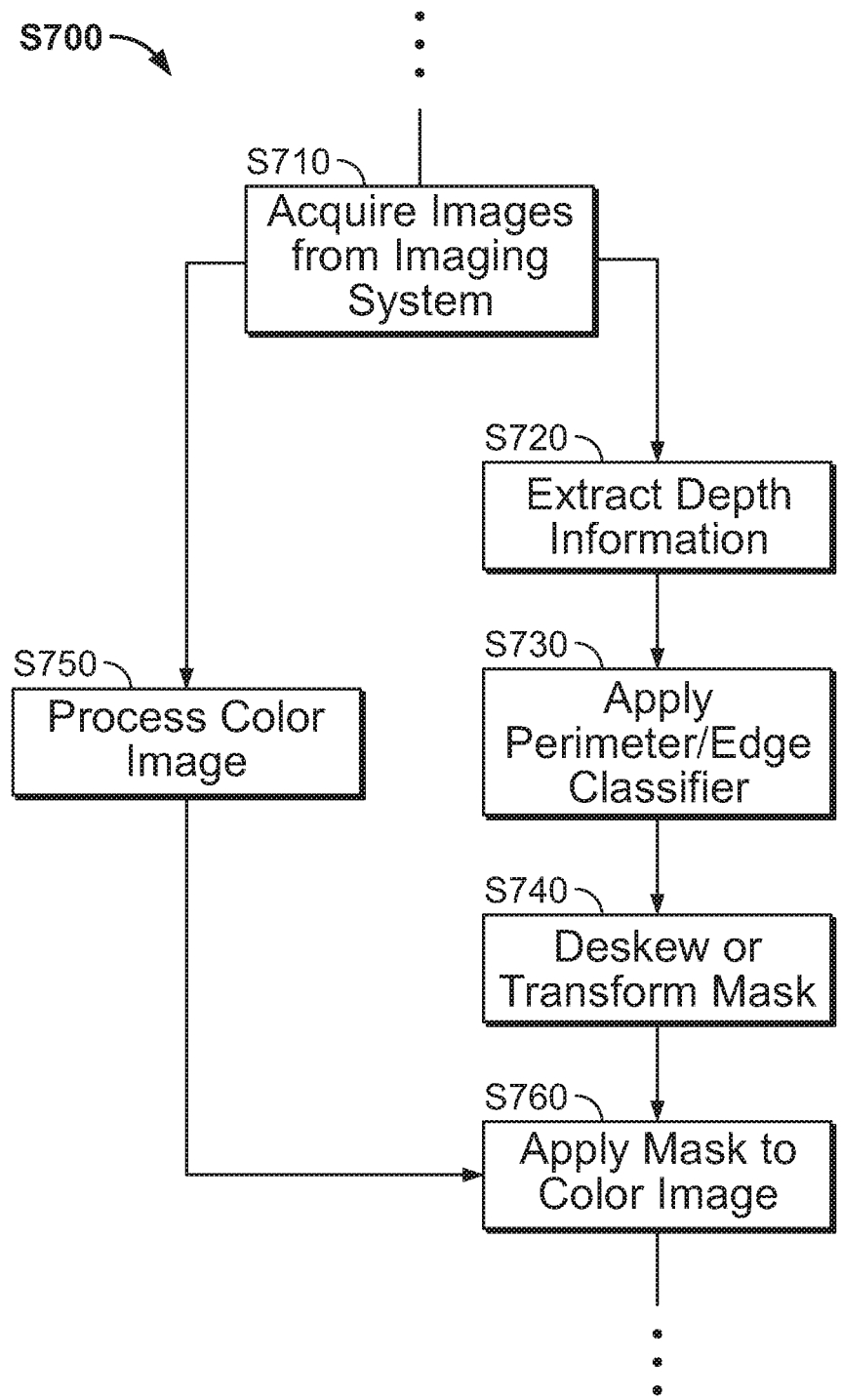
FIG. 7 is a flowchart representation of a method for generating an image mask.

In some variations, to facilitate computational speed, efficiency and/or accuracy, a method S700 to create and apply a mask to the color image may be optionally used. For example, in FIG. 7, the depth imaging system 122 may be used to obtain a depth image S710 along with an associated image from the color imaging system 120. The depth channel information is then extracted or obtained at S720, derived or calculated from the infrared image if needed. At S730, the perimeter or edge classifier, which may be similar or the same as the perimeter or edge classifier at S 220, may be used to identify the perimeter of the surgical textile. The image may then be deskewed or transformed at S740, if needed, to the perspective of coordinate system of the color image as described elsewhere herein. The color image may also be processed for color and/or contrast normalization at S750, e.g. generating a histogram distribution or color curve of the RGB channel and normalizing the color image to a different histogram or curve. The corresponding to the surgical textile image is then applied as mask to the color image at S760, to exclude any background color pixels from unnecessary analysis.

Figure 8:
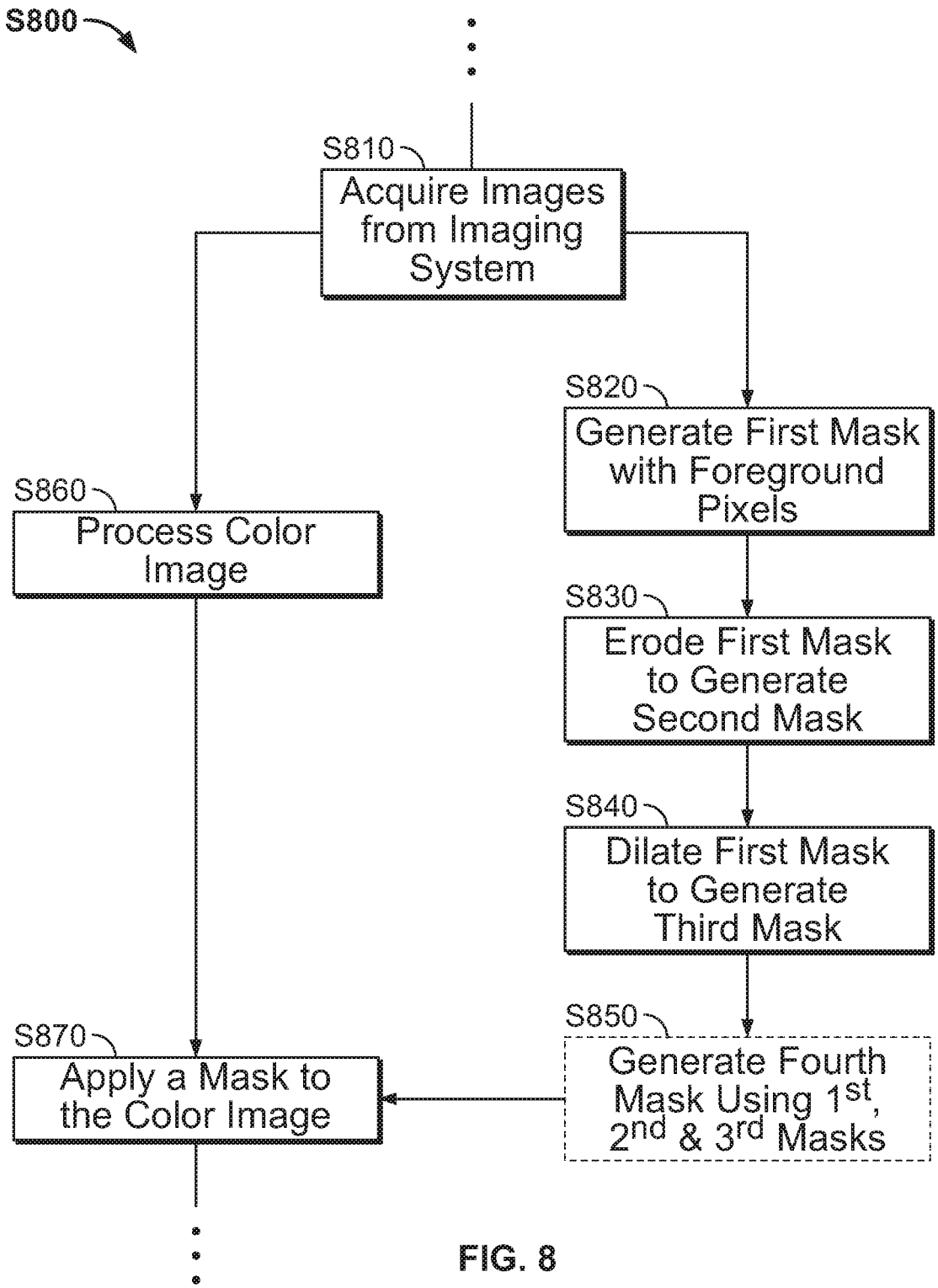
FIG. 8 is another flowchart representation of a method for generating an image mask using erosion and dilation processing.

In another example of a mask method S800, depicted in FIG. 8, a depth image and color image are obtained from the infrared system and color system at S810. At S810, a first mask is generated from the depth channel of the infrared image by treating maximum foreground pixel values as positive and all other pixels as negative, which may be the result of the surgical textile being presented to the IR camera at or below the IR camera's minimum depth range. At S830 and S840, the first mask undergoes erosion and dilation, which are threshold-based morphological image processing operations that may be used to reduce noise and false negative pixels. For example, to perform the erosion, each pixel in the mask is replaced with the minimum value of the surrounding pixels, which may be configured or defined as a 3×3 or 5×5, 7×7, 3×5, or 5×3 pixel zone or window, for example. This erosion process may be applied to the first mask to generate a second mask, either as a single pass or via multiple passes, and different pixel windows may be used on different passes. This erosion process may be used reduce the background noise or other false positive pixels in the first mask. Next, a dilation process may be applied to the first mask to generate a third mask, wherein each pixel in the first mask is replaced with the maximum value in a group of surrounding pixels, e.g. 3×3 or 5×5, 7×7, 3×5, or 5×3 pixel zone or window. The grouping may be the same or may be different than the grouping used for the erosion process, and may also be performed in a single pass or multiple passes, with the same or different grouping for each pass. This dilation process may be used to potentially turn back on certain false negative pixels. Using these three masks, at S850 fourth mask with 2-bit per mask pixel may be optionally be generated wherein all pixels from the second mask are flagged as "11" or otherwise as definite foreground pixels. Any pixels not in the third mask are flagged as "00" or otherwise definite background pixels. Any pixels in the first mask but not in the second mask are labeled "10" as probable foreground pixels, and any pixels in the third mask but not in the first mask is labeled "01" or probable background pixels.

Depending upon the desired sensitivity and/or specificity needed, the first, second or fourth mask may be used to identify the corresponding pixels in the color image for further processing. In masks such as the first or fourth mask, additional processing, such as perimeter or edge detection may be applied to further refine the mask before application to the color image.

10. Hand Removal

The computing device may also identify regions of the color image corresponding to a user's hands—holding the surgical sponge—and discard these regions from processing in Blocks S140 and S150. For example, the computing device may: scan a selected region of the depth map in a frame pair confirmed as representative of a surgical sponge; correlate an area within the depth image proximal a corner of this selected region and exhibiting reduced distance from the imaging system with a hand; and then designate the corresponding area in the color image for removal from processing in Block S140. The computing device may also remove this area from an outline of a surgical sponge shown on the display. The computing device may apply the foregoing methods and techniques to a frame pair designated for processing only after a surgical sponge has been confirmed in the field of view of the imaging system. Alternatively, the computing device may apply the foregoing methods and techniques to each frame pair and to each depth image or color image rendered on the display.

11. Blood Component Quantity and Sponge Counter

In Block S140, once a color image confirmed as containing a region representative of a sufficiently planar surgical sponge within a suitable distance of and suitably normal to the field of view of imaging system is captured and recorded, the computing device can implement methods and techniques as described in U.S. patent application Ser. No. 13/544,664, which is hereby incorporated by reference in its entirety, to transform color values contained in pixels in the color image into an estimation of the mass, volume, or other quantitative measurement of the amount of whole blood, red blood cells, hemoglobin, and/or other blood component in the real surgical sponge represented in the color image.

In some variations, prior to transforming pixel color values to an estimation of a blood component value, the image (with or without any masking described herein), may also undergo ambient light correction as described in U.S. patent application Ser. No. 15/154,917, which is hereby incorporated by reference in its entirety.

In Block S150, the computing device may also implement methods and techniques as described in U.S. patent application Ser. No. 13/544,664 to index a counter representative of the total number of surgical sponges identified and counted during an operation in which the computing device is in operation. In this variation, the computing device may render a value contained in the sponge counter on the display and update this rendered value substantially in real-time once a surgical sponge is confirmed in the field of view of the imaging system. For example, the computing device can flash an updated sponge counter value on the display when a surgical sponge is confirmed and counted. Similarly, when a possible surgical sponge is detected in a frame pair, the computing device can overlay a next sponge counter value (i.e., a current sponge count+1) over a depth (or color) image rendered on the display, and the computing device can increase the opacity of the overlaid sponge counter value as the value in the frame counter increases for subsequent frame pairs.

In another embodiment, a color image, after segmentation of the surgical textile, is further segmented or masked based upon the regions of image comprising blood, to exclude non-blood regions of the surgical sponge. This may be performed by using a rule-based algorithm below, $s=r_{i,j}+g_{i,j}+b_{i,j}$ where r, g and b correspond to the red, green and blue channels of the image of the pixel at i,j location in the image:

If $$\left(\frac{r_{i,j}}{s} < X \cap \left(\frac{g_{i,j}}{s} > Y \cup \frac{b_{i,j}}{s} > Z\right)\right)$$

then remove or mask $p_{i,j}$, else include,

Where X is in the range of about 105 to about 150, Y is in the range of about 60 to about 70, and Z is in the range of about 60 to about 70.

12. Vocal Sponge Count

In one variation, the computing device may capture and store audio data with images and blood component quantity data for surgical sponges detected and imaged during operation. In particular, the computing device can record users (e.g., two users, such as nurses, anesthesiologists, technicians, etc.) sequentially reciting a vocalized sponge count.

In one implementation, when a possible sponge is detected in a frame pair and the frame counter indexed to 1, the computing device may initiate an audio recording by sampling a microphone connected to or integrated into the computing device. Subsequently, if the value of the frame counter reaches the threshold value and a surgical sponge thus confirmed, the computing device can continue the audio recording until the earlier of five seconds after: the sponge is confirmed; and a new sponge is detected in the field of view of the imaging system. The computing device can then store and link this audio recording with the corresponding color image of the surgical sponge. For example, the computing device can record a color image of a surgical sponge, transform the color image into an estimation of a blood component quantity (e.g., a volume of hemoglobin) in the surgical sponge; and store this color image and the blood component quantity estimation with a time the image was captured, a sponge counter value for the surgical sponge, and an audio recording of two users reading and confirming the count value of the sponge.

In another implementation, the computing device may record a single audio track throughout an operation and then splice the audio track into multiple discrete audio segments, match each audio segment to a recorded color image and a blood component quantity estimation based on a time of the audio segment and a time the color image was captured, and then store each audio segment with a tag or other pointer to its corresponding color image or related data.

12. Duplicate Sponge Rejection—RFID

In one variation, the computing device further includes a radio-frequency identification ("RFID") reader and RFID antenna. In this variation, once the computing device indexes the image counter to "1" (or to some other value less than the threshold value) to indicate a possible surgical sponge in the field of view of the imaging system, the computing device can broadcast an excitation signal through the RFID antenna and then sample the RFID reader. If the sponge in the field of the view of the imaging system includes an RFID tag, this RFID tag can broadcast a data packet back to the RFID reader. The computing device can apply receipt of this data packet from the surgical sponge to confirm the sponge and then capture and process the color image of the sponge as soon as planarity, distance, position, and/or other requirements are met, as described above, and before the image counter reaches the threshold. The computing device can additionally or alternatively implement supervised machine learning techniques to train optical sponge detection models based on this RFID data packet received from the surgical sponge and depth maps and/or color images of the surgical sponge. Alternatively, the computing device can broadcast an excitation signal and read an incoming data packet from a nearby sponge only once the frame counter reaches the threshold value and the surgical sponge is thus confirmed optically.

In the foregoing implementation, the computing device may compare an RFID data packet received from a current surgical sponge to data packets previously received from other sponges during an operating period in order to detect a duplicate scan of the same surgical sponge. In particular, if the RFID data packet received from the surgical sponge is identical to an RFID data packet previously received during the same operating period, the computing device can reject the surgical sponge as a duplicate, discard the corresponding frame pair, and discard a blood component quantity estimation for the surgical sponge.

Furthermore, in this variation, in order to prevent detection of other nearby RFID tags, the computing device can vary the power output of the RFID antenna according to a distance between the computing device and the sponge estimated from a current depth map. In particular, the computing device can translate a distance value in a region of the current depth map corresponding to a possible or conformed surgical sponge into a power level of an excitation signal to be subsequently broadcast by the RFID antenna. However, in this variation, if no data packet is received following transmission of an excitation signal, the computing device can proceed according to Blocks of the method described above in order to confirm the surgical sponge and to process a color image of the sponge. Furthermore, if an RFID data packet is not received following broadcast of an excitation signal, the computing device can tag the surgical sponge (e.g., the sponge counter value of the surgical sponge, the color image of the surgical sponge, etc.) as not RFID-enabled.

In further examples, the computing device may also identify any barcode, QR code or other visual code on the surgical textile. For example, the processor may scan the color image for the four corners of the QR code or barcode, and then identify the coded region. At block S410, the processor then decodes the coded region to determine the code string. The code string may then be used to uniquely identify the detected surgical textile, to avoid double-counting if the same surgical textile is presented again to the system, and to provide a warning to the user or surgeon.

13. Duplicate Sponge Rejection—Reflective IR Coating

In another variation, the computing device implements machine vision techniques to detect a reflective material on a surgical sponge depicted in a frame pair and identify the sponge (uniquely) based on the detected reflective material. For example, the computing device can include a second IR emitter configured to illuminate the field of view of the IR camera with electromagnetic radiation both reflected by material printed onto or sewn into surgical sponges and detected by the IR camera. During a sampling period, the computing device can thus capture and process a second infrared image to detect a standard or substantially unique pattern of reflective material within a surgical sponge in the field of view of the imaging system. The computing device may then implement methods and techniques described above to confirm presence of a surgical sponge in the field of view of the imaging system, to uniquely identify the image based on the pattern of reflective material, to reject duplicate surgical sponges, to trigger early capture and processing of a color image of the surgical sponge, and/or to improve an optical surgical sponge detection model according to supervised machine learning techniques, etc.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

In the present description, the terms component, module, device, etc. may refer to any type of logical or functional circuits, blocks and/or processes that may be implemented in a variety of ways. For example, the functions of various circuits and/or blocks can be combined with one another into any other number of devices. Or, the devices can comprise programming instructions transmitted to a general purpose computer or to processing/graphics hardware via a transmission carrier wave. Also, the devices can be implemented as hardware logic circuitry implementing the functions encompassed by the innovations herein. Finally, the devices can be implemented using special purpose instructions (SIMD instructions), field programmable logic arrays or any mix thereof which provides the desired level performance and cost.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other variations for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on As a person skilled in the art will recognize from the previous detailed description and from the figures and claims, modifications and changes can be made to the embodiments of the invention without departing from the scope of this invention as defined in the following claims.

The preceding description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

What is claimed is:

1. A system for measuring blood content, comprising:
   a color imaging system configured to acquire a color image of a field of view comprising a surgical textile;
   an infrared imaging system configured to acquire an infrared image of the field of view;
   a processor configured to:
      determine depth information for the surgical textile from the infrared image;
      identify surgical textile pixels in the color image; and
      extract blood information from the surgical textile pixels.

2. The system of claim 1, wherein the processor is further configured to transform the infrared image to a coordinate system corresponding to the color image.

3. The system of claim 1, wherein the processor is further configured to generate a depth image from the infrared image.

4. The system of claim 3, wherein the processor is further configured to identify a planar set of pixels in the depth image.

5. The system of claim 4, wherein the processor is further configured to detect a surgical textile image perimeter in the depth image.

6. The system of claim 5, wherein the detection of the surgical textile image perimeter is performed by looking for a sharp vertical depth drop-off in the depth image.

7. The system of claim 3, wherein the processor is further configured to downsample the depth image or the infrared image.

8. The system of claim 7, wherein the processor is further configured to generate a mask image from the downsampled depth image.

9. The system of claim 8, wherein the processor is further configured to upsample the mask image.

10. The system of claim 1, wherein the processor is further configured to perform fill-in of a missing infrared pixel region in the infrared image.

11. The system of claim 5, wherein the processor is further configured to generate a mask image using the detected perimeter.

12. The system of claim 11, wherein the processor is further configured to transform the mask image to a coordinate system of the color image.

13. The system of claim 11, wherein the detected perimeter is a top edge and a bottom edge of a surgical textile image.

14. The system of claim 11, wherein the detected perimeter comprises opposing edges of a surgical textile image.

15. The system of claim 11, wherein the detected perimeter comprises corners of a surgical textile image.

16. The system of claim 1, wherein the processor is further configured to index a frame counter upon generating shape information that is characteristic of the surgical textile.

17. A computer-implemented method of analyzing an object containing a blood component, comprising:
    acquiring a depth image and a color image of a field of view;
    using the depth image to determine the presence of a surgical textile in the field of view; and
    using the color image to estimate a characteristic of a blood component contained in the surgical textile.

18. The method of claim 17, further comprising:
    generating an image mask using the depth image; and
    applying the image mask to the color image to eliminate background pixels.

19. The method of claim 18, further comprising applying at least one of erosion and dilation image processing to the depth image.

20. A computer-implemented method of performing fluid monitoring, comprising:
    acquiring a depth image of a surgical textile in a field of view;
    acquiring a color image of the surgical textile in the field of view;
    generating an image mask using the depth image; and
    using the image mask with the color image to identify a region of the color image corresponding to the surgical textile.

21. The method of claim 20, further comprising transforming the infrared image to the geometry perspective of the color image.

22. The method of claim 20, further comprising downsampling the infrared image prior to generating the image mask.

23. The method of claim 22, further comprising upsampling the image mask before using the image mask to identify the region of the color image.

* * * * *